United States Patent
Hashimoto et al.

[11] Patent Number: 5,393,369
[45] Date of Patent: Feb. 28, 1995

[54] ETCHING RATE DETERMINING METHOD AND APPARATUS

[75] Inventors: Shigeo Hashimoto; Shogo Kawasaki, both of Hirakata, Japan

[73] Assignee: C. Uyemura & Co., Ltd., Osaka, Japan

[21] Appl. No.: 939,711

[22] Filed: Sep. 2, 1992

[30] Foreign Application Priority Data

Sep. 5, 1991 [JP] Japan .................. 3-254792

[51] Int. Cl.⁶ .............................. C23F 1/00
[52] U.S. Cl. .................. 156/626; 156/664; 156/345
[58] Field of Search ............... 156/627, 626, 665, 664, 156/345; 204/129.2

[56] References Cited

U.S. PATENT DOCUMENTS

| | | | |
|---|---|---|---|
| 2,180,798 | 11/1939 | Collins | 156/626 |
| 2,827,724 | 3/1958 | Edds | 156/626 |
| 3,503,817 | 3/1970 | Radimer | 156/626 |
| 4,137,047 | 1/1979 | Kim | 436/62 |
| 4,388,276 | 6/1983 | Konstantouros et al. | 156/642 X |

FOREIGN PATENT DOCUMENTS 603702 4/1978 U.S.S.R. ................ 156/626

OTHER PUBLICATIONS

Derwent Publication Abstract No. 87-191208/27 (Nov. 1986).
Derwent Publication Abstract No. 08876 (Feb. 1982).
Derwent Publication Abstract No. 88-073475 (Feb. 1988).
Derwent Publication Abstract No. 89-247108 (Nov. 1988).
Derwent Publication Abstract No. 92-231487 (May 1992).

*Primary Examiner*—Thi Dang
*Attorney, Agent, or Firm*—Birch, Stewart, Kolasch & Birch

[57] ABSTRACT

A process and apparatus for monitoring the etching ability of an etchant by accurately measuring the etching rate with a relatively simple arrangement. A process and apparatus for monitoring the etching rate is determined by channeling the etchant from an etching tank to a reaction column, subjecting a specimen of the same material as a metal part to be etched in practice to etching with the etchant in the reaction column, collecting hydrogen gas generated during etching of the specimen, measuring the time taken until a predetermined quantity of hydrogen gas is generated, and computing the etching rate from the measured time.

4 Claims, 2 Drawing Sheets

ETCHING RATE DETERMINING METHOD AND APPARATUS

BACKGROUND OF THE INVENTION

1. Field of the Invention

This invention relates to a method and apparatus for determining an etching rate. More particularly, it relates to a method and apparatus for determining the etching rate at which light metals and alloys thereof, such as aluminum, aluminum alloys, magnesium and magnesium alloys, are etched with acid or alkali etchants.

2. Description of the Related Art

In the etching art, aluminum parts are often subject to a pretreatment by immersing them in acid or alkali liquid etchants for etching the surface thereof prior to customary surface treatments, like anodizing and plating. For such a pretreatment, it is desired in view of management of the etchant to monitor the etching ability of the etchant by measuring the etching rate.

Several techniques are known for the measurement of etching rate, including a weighing technique for measuring the quantity (in mg unit) of metal etched away per unit time, and a coulostatic technique of applying a potential to an electrode immersed in the etchant, and measuring the time taken until the potential becomes constant.

However, the weighing technique presents a problem in that, because measurement cannot be carried out in a reaction system for actual treatment, another system containing a measurement specimen must be used for measurement, from which the etching rate associated with actual etching can only be presumed. This can lead to a time lag, and requires a large sized measuring system. The coulostatic technique also requires a large apparatus, and increases the cost of etching rate measurement.

SUMMARY OF THE INVENTION

Therefore, an object of the present invention is to provide a method for accurately determining an etching rate with minimal measurement errors, such as time lag. Another object is to provide a relatively simple and inexpensive apparatus capable of such accurate determination of the etching rate.

Seeking a method for measuring the etching rate at which a metal part is etched with an acid or alkali etchant in an etching tank, wherein the metal generates hydrogen gas when etched with said etchant, we have found that the etching rate can be determined by sampling a portion of the etchant from the etching tank, containing the metal part to be etched etching a specimen of the same material as the metal part to be etched with the sampled portion of the etchant, collecting hydrogen gas generated from the specimen as a result of this etching, measuring the time taken until the quantity of hydrogen gas generated reaches a predetermined level, and computing the etching rate from the measured time.

The means for collecting the hydrogen gas generated with the progress of etching and measuring the time taken until the predetermined quantity of hydrogen gas is generated may comprise a reaction column of the closed type, adapted to carry out etching of the specimen, and a metering column for measuring the quantity of hydrogen gas generated, with both of the columns connected for fluid communication. With this arrangement, the etchant is first channeled from the etching tank into the reaction column, where the specimen is subject to etching with the etchant. The etchant is then channeled from the reaction column into the metering column due to an increase in the interior pressure of the reaction column as a result of hydrogen gas generation during etching. There is further provided a means for measuring the time taken until the etchant in the metering column has increased by a predetermined quantity. Then the time taken for the generation of a unit quantity of hydrogen gas can be accurately measured by a relatively simple arrangement.

Accordingly, the present invention provides a method for determining the etching rate at which a metal part is being etched with an acid or alkali etchant in an etching tank, wherein the metal generates hydrogen gas when etched with the etchant. The method includes the steps of: channeling the etchant from the etching tank containing a metal part to be etched to a reaction column, subjecting a specimen of the same material as the metal part to etching with the etchant in the reaction column, collecting hydrogen gas generated during etching of the specimen, measuring the time taken until a predetermined unit quantity of hydrogen gas is generated, and computing the etching rate from the measured time.

In a second aspect, the invention provides an apparatus for determining the etching rate at which a metal part is etched with an acid or alkali etchant in an etching tank, wherein the metal generates hydrogen gas when etched with the etchant. A reaction column of the closed type is adapted to accommodate therein a specimen of the same material as the metal part to be etched and to receive the etchant from the etching tank, whereby the specimen is subject to etching with the etchant in the reaction column. A metering column is connected to the reaction column in such a way that the etchant is introduced into the metering column from the reaction column as the interior pressure of the reaction column increases. A flow control mechanism for controlling the inflow and outflow of the etchant into and from the respective columns operates such that the etchant is channeled from the etching tank to the reaction column, whereby the specimen is subject to etching with the etchant in the reaction column and the etchant is then channeled from the reaction column into the metering column due to an increase in the interior pressure of the reaction column as a result of hydrogen gas generation during etching. The metering column is provided with means for measuring the time taken until the etchant in the metering column reaches a predetermined quantity.

Further scope of applicability of the present invention will become apparent from the detailed description give hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings, which are given by way of illustration only, and thus are not limitative of the present invention, and wherein.

DETAILED DESCRIPTION OF THE INVENTION

The etching rate determining method of the present invention is useful for determining the etching rate associated with a process for etching parts of metallic material, such as aluminum, aluminum alloys, magnesium, and magnesium alloys, with an acid or alkali liquid etchant in an etching tank, wherein the metallic material generates hydrogen gas when etched with such etchant. A specimen formed of the same material as the metal part to be etched in the etching tank is etched with the etchant sampled from the etching tank. The time taken until a predetermined unit quantity of hydrogen gas is generated is measured (which time is referred to as a unit quantity hydrogen release time, hereinafter). The etching rate is computed from the measured time.

Figure 1:
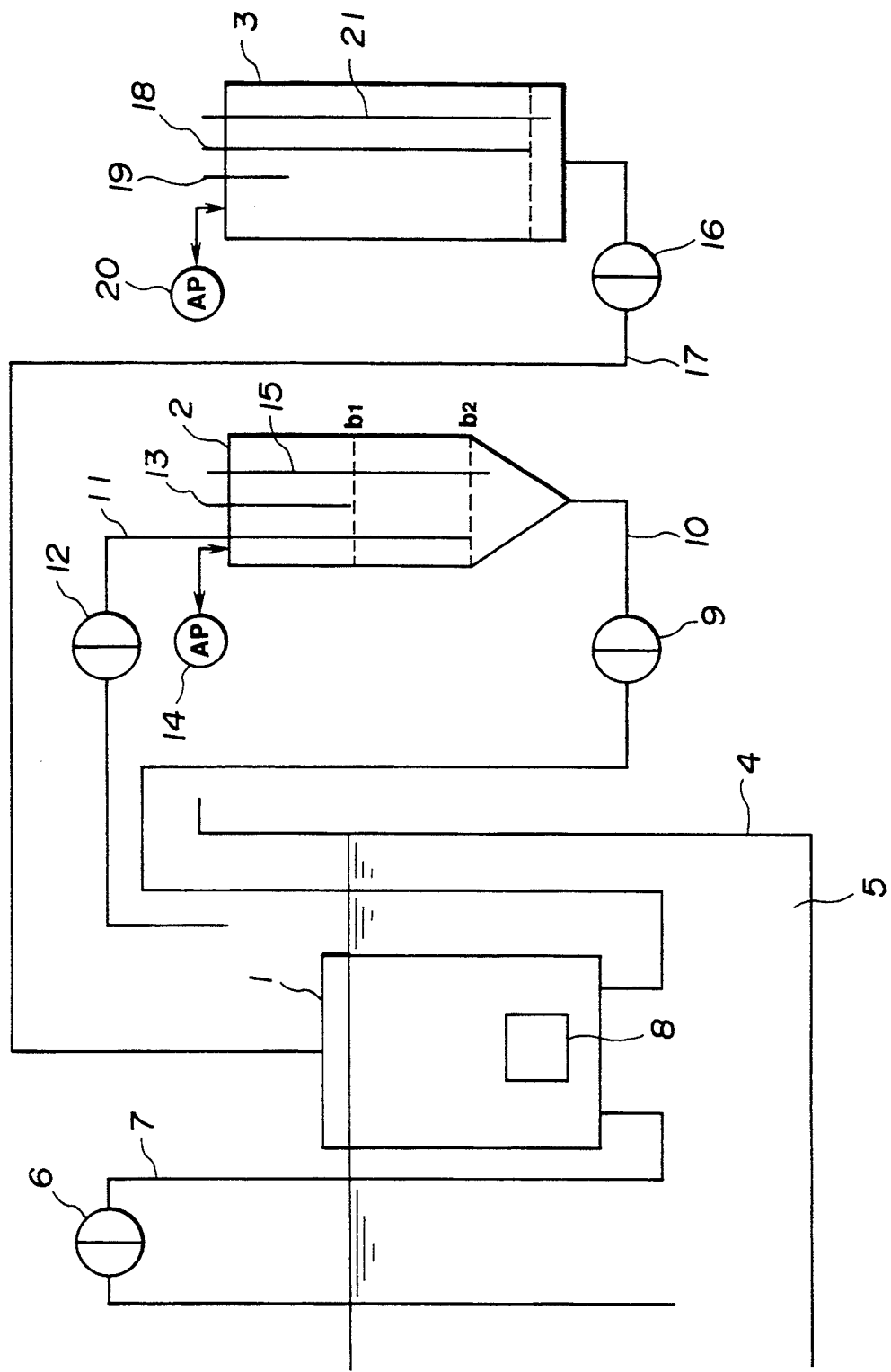
FIG. 1 is a schematic view of an etching rate determining apparatus according to one embodiment of the invention.

Referring to FIG. 1, there is illustrated an etching rate determining arrangement according to one embodiment of the invention, by which the unit quantity hydrogen release time can be measured in a simple manner. The apparatus generally includes a reaction column 1, a metering column 2 and a priming or suction column 3.

An etching tank 4 is partially illustrated as containing a liquid etchant 5 to be examined for etching rate, so that metallic parts (not shown) may be actually etched in the tank 4. The reaction column 1 is of the closed box type and half immersed in the etchant 5 in the tank 4. To the bottom of the reaction column 1 is connected an etchant inlet line 7 having a valve 6. The distal end of the line 7 is immersed in the etchant 5 in the tank 4. In the reaction column 1 is disposed a specimen 8 which is formed of the same material as the metallic parts to be etched in the tank 4.

The metering column 2 is a cylinder column which at the bottom is in communication with the bottom of the reaction column 1 through a feed line 10 having a valve 9. A return line 11 is inserted into the metering column 2 such that its proximal end is located at a lower level b2 in the metering column 2. The return line 11 has a valve 12 at an intermediate point, and a distal end disposed above the etching tank 4. Disposed in the metering column 2 is a liquid level sensor 13 which has a sensitive end located at an upper level b1 in the metering column 2 and a common level 15 located deep enough in the metering column 2. Further a first air pump 14 is coupled to the top of the metering column 2.

The bottom of the priming column 3 is in fluid communication with the top of the reaction column 1 through a line 17 having a valve 16. Disposed in the priming column 3 are a first liquid level sensor 18 having a sensitive end located at a lower level in the column and a second liquid level sensor 19 having a sensitive end located at an upper level in the column and a common level 21 located deep enough in the column 3. A second air pump 20 is coupled to the top of the priming column 3.

Figure 2:
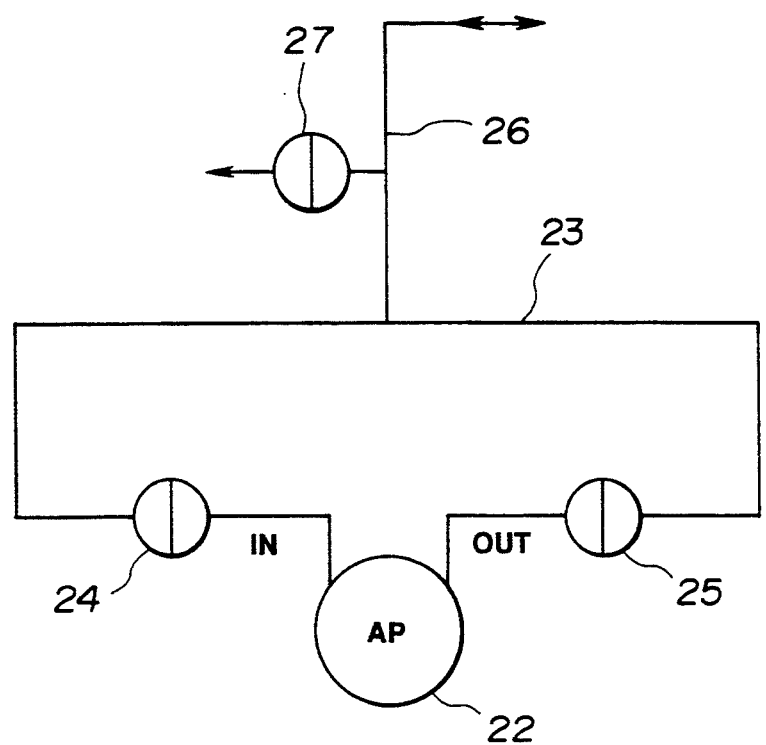
FIG. 2 is a schematic view of the air pump used in the apparatus of FIG. 1.

The first and second air pumps 14 and 20 each are of the arrangement shown in FIG. 2. The pump includes a pump body 22 having suction and discharge ends connected through a loop line 23. Valves 24 and 25 are disposed in the loop line 23 near the suction and discharge ends, respectively, and a coupling line 26 is connected to the loop line 23 intermediate the valves 24 and 25. The coupling line 26 is connected to the metering or priming column 2 or 3. An air venting valve 27 is connected to the coupling line 26.

With the vent valve 27 closed, the air pump of this arrangement can be a suction pump when the valve 25 is closed and the valve 24 is opened, but a discharge pump when the valve 25 is opened and the valve 24 is closed. It is to be noted that the manipulation of these valves during operation of the first and second air pumps 14 and 20 for suction or discharge of air is omitted from the following description.

With this arrangement, the unit quantity hydrogen release time is measured by first actuating the second air pump 20 for sucking and evacuating the air from the priming column 3 with the valves 6 and 16 opened. Then the liquid etchant 5 in the etching tank 4 is channeled to the reaction column 1 through the inlet line 7 and after the reaction column 1 is filled with the etchant, the etchant is further channeled to the priming column 3 through the line 17. When the first level sensor 18 detects the surface of the etchant, the second air pump 20 is interrupted and the valve 16 is closed. Then the reaction column 1 is full of the etchant to be examined.

Next, with the valve 6 kept open, the valve 9 is opened and the first air pump 14 is actuated for sucking and evacuating the air from the metering column 2. Then the etchant in the reaction column 1 is passed to the metering column 2 through the feed line 10. When the level sensor 13 detects the surface of the etchant in the metering column 2, the first air pump 14 is interrupted and the valve 9 is closed. Then the metering column 2 is full of the etchant to the height b1 corresponding to the detecting end of the sensor 13. Since this operation is carried out with the valve 6 opened, the reaction column i is continuously replenished with the etchant from the tank 4 in an amount corresponding to the amount that has transferred from the reaction column 1 to the metering column 2.

Next, with the valve 9 closed, the valve 12 is opened, the first air pump 14 is actuated to pump air into the metering column 2 to pressurize the interior thereof. Then the etchant in the metering column 2 is forced back to the tank 4 through the return line 11 until the surface of the etchant in the metering column comes down to the height b2 corresponding to the distal end (detecting end) of the return line 11. The arrangement is now ready for measurement.

Next, the valve 6 is closed and the valve 9 and the air vent valve 27 associated with the first air pump 14 (see FIG. 2) are opened for starting measurement. Then the specimen 8 is etched with the etchant in the reaction column 1, where hydrogen gas generates during etching so that the reaction column 1 increases its interior pressure. In response to the increasing interior pressure, that is, the quantity of hydrogen gas generated, the etchant in the reaction column 1 is purged to the metering column 2 through the feed line 10. A timer (not shown) is used to measure the time taken until the surface of the etchant in the metering column 2 rises from level b2 to level b1. The point of time when the etchant reaches level b1 can be detected by the liquid level sensor 13.

By measuring the time taken until the surface of the etchant in the metering column 2 rises from level b2 to level b1 in this way, the time taken for releasing a quantity (unit quantity) of hydrogen gas equal to the volume of the region of the metering column 2 between levels b2 and b1 can be readily and accurately obtained.

In the above-mentioned arrangement, measurement is done with the reaction column 1 partially immersed in the etchant 5 in the tank 4 so that the etching for measurement is effected under the same temperature condition as the actual etching, ensuring very accurate measurement. Automatic measurement is possible by using a programmed computer control for controlling the relevant operations including valve operation, air pump actuation, and time measurement and the;calculation to be described later may also be carried out by the same computer, resulting in fully automatic measurement. Of course, these operations may be carried out manually, if desired.

According to the etching rate determining method of the invention, the etching rate is computed from the unit quantity hydrogen release time obtained by the above-mentioned procedure or the like. The following computing factors are necessary, other than the time.

P: atmospheric pressure (atm)
V: unit volume (liter) (corresponding to the volume between b2 and b1 in metering column 2 in the above-illustrated procedure)
T: temperature (K)
S: surface area of specimen (cm$^2$)

For example, the etching rate v ($\mu$m/hr) for aluminum may be computed from these computing factors and the unit quantity hydrogen release time t (sec) in accordance with the following formula.

The hydrogen gas generation associated with etching of aluminum with acid is represented by the reaction formula:

$$Al + 3H^+ \rightarrow Al^{3+} + 3/2 H_2$$

Aluminum molecular weight: 26.98154 g/mol
Aluminum density: 2.6988 g/cm$^3$
Aluminum volume per mol: 99966.6 cm$^2 \cdot \mu$m
Provided that hydrogen gas follows PV=nRT wherein n is moles and R is a constant equal to 0.08211, then the mole number m of aluminum is given by $$m = (2/3) PV/RT.$$

The quantity d of aluminum etched is $$d = 99966.6 \, m/S$$

wherein S is the surface area of the specimen.
Then, the etching rate v ($\mu$m/hr) is

$$v = d \times 3600/t$$
$$= 2.922 \times 10^9 \times PV/TSt$$

wherein t is a measured time.

In this regard, the etching rate computed by the inventive method may contain errors which are caused by various factors including (1) a time lag associated with liquid surface detection by the level sensor, (2) dissolution of hydrogen gas in the etchant, (3) pressure variations (including atmospheric pressure variation, tank liquid surface variation, and column height variation), (4) specimen thickness reduction, (5) concentration variation in the reaction column, (6) temperature changes and the like. The error factors may be accommodated as follows.

(1) Time Lag Associated with Liquid Surface Detection by the Level Sensor

The time lag can be made negligible by carrying out measurement on a minute basis.

(2) Dissolution of Hydrogen Gas in the Etchant

It need not be taken into account where the etching tank is operating in practice, because the etchant is saturated by hydrogen at a steady state. If the etching tank is quiescent, a correction may be made in accordance with the solubility and dissolving rate of hydrogen, but such a correction is not necessary in most cases.

(3) Pressure Variations (Including Atmospheric Pressure Variation, Tank Liquid Surface Variation, and Column Height Variation)

The major cause of pressure variation is an atmospheric pressure variation which is approximately equal to 1% at 10 millibar. The error caused by column height variation is about 1% at a height variation of 10 cm, but no error is introduced if the pressure within the reaction column is measured and used for computation.

(4) Specimen Thickness Reduction

For a specimen dimensioned 10×10×1 mm and an etching rate of 25 $\mu$m/hr, 10 hours etching results in a specimen thickness reduction of 0.5 mm or an area reduction of about 8.3%. This factor can be eliminated by forming the specimen in plate shape, and coating the edges of the specimen, thereby reducing the surface area reduction by etching, or alternatively, computing a surface area change from the measured etching rate and making a correction using it.

(5) Concentration Variation in the Reaction Column

The concentration varies over 10% when the ratio of S/V (surface area/volume) of the specimen is 1 dm$^2$/liter. This can be eliminated by increasing the S/V ratio. Alternatively, the average rate may be determined by setting the S/V ratio equal to that of a metallic part to be etched in practice.

(6) Temperature Changes

A temperature change of 3% leads to an error of 1%. Such an error can be eliminated by measuring the temperature in the reaction column and using the measured temperature for computation.

In the practice of the inventive method, the measurement of the time taken until the predetermined unit quantity of hydrogen gas is generated is not limited to the above-mentioned arrangement and measurement may be made by any suitable method. Also changes may be made to the elements of the measuring arrangement. For example, the metering column 2 may be a measuring cylinder as in the Example described below whereupon an increase of liquid volume in the metering column can be visually determined. The mechanism for channeling the etchant into the reaction column 1 need not use the priming column 3 or an arrangement may be made such that the etchant is channeled directly into the reaction column 1.

EXAMPLE

An example is given below by way of illustration and not by way of limitation.

Using the arrangement shown in FIG. 1, the etching rate of an etchant with respect to aluminum was measured. The etchant used was "Mill Etch" (trade name).

The specimen 8 was an aluminum plate of 10×10×1 mm (surface area 2.4 cm²). The reaction column 1 had a volume of 25.5 ml. The metering column 2 was a measuring cylinder having a measurable volume of 10 ml. The time corresponding to a liquid increment of 1 ml in the measuring cylinder was measured. The etching rate was computed in accordance with the following formula. The results are shown in Table 1.

$$v = 2.922 \times 10^9 \times PV/(T \cdot S \cdot t)$$

P: atmospheric pressure (atm)
V: unit volume (liter)
T: temperature (K)
S: surface area of specimen (cm²)
t: measured time (sec)

An aluminum part of 10×10×1 mm was etched with the same etchant before the etching rate was measured by the same procedure as above. This etching procedure was repeated 4 times in total. The results at the end of each procedure are shown in Tables 2 to 4.

It is to be noted that in Tables 2 to 4, the outlet height refers to the difference height between the reaction column 1 and the metering column 2. An error caused by a differential pressure resulting from the outlet height is eliminated by measuring the pressure within the reaction column 1 and using this pressure for computation of the etching rate.

TABLE 1

|      | Time (sec) | Total (sec) | Rate (μm/hr) |
|------|------------|-------------|--------------|
| 1 ml | 173 | 173 | 28.43 |
| 2 ml | 183 | 356 | 26.88 |
| 3 ml | 189 | 545 | 26.03 |
| 4 ml | 191 | 736 | 25.75 |
| 5 ml | 197 | 933 | 24.97 |
| 6 ml | 197 | 1130 | 24.97 |
| 1–6 ml | 1130 | — | 26.11 |
| 2–6 ml | 957 | — | 24.32 |

TABLE 2

2nd, specimen exchanged 2.38 cm², outlet height 72 mm

|      | Time (sec) | Total (sec) | Rate (μm/hr) |
|------|------------|-------------|--------------|
| 1 ml | 153 | 153 | 27.02 |
| 2 ml | 165 | 318 | 25.05 |
| 3 ml | 167 | 485 | 24.75 |
| 4 ml | 165 | 650 | 25.05 |
| 5 ml | 168 | 818 | 24.61 |
| 1–5 ml | 818 | — | 25.26 |
| 2–5 ml | 665 | — | 24.86 |

TABLE 3

3rd, outlet height 155 mm

|      | Time (sec) | Total (sec) | Rate (μm/hr) |
|------|------------|-------------|--------------|
| 1 ml | 155 | 155 | 26.67 |
| 2 ml | 169 | 324 | 24.46 |
| 3 ml | 170 | 494 | 24.32 |
| 4 ml | 169 | 663 | 24.46 |
| 5 ml | 172 | 835 | 24.03 |
| 1–5 ml | 835 | — | 24.75 |
| 2–5 ml | 680 | — | 23.89 |

TABLE 4

4th, outlet height 69 mm

|      | Time (sec) | Total (sec) | Rate (μm/hr) |
|------|------------|-------------|--------------|
| 1 ml | 161 | 161 | 25.68 |
| 2 ml | 170 | 331 | 24.32 |
| 3 ml | 170 | 501 | 24.32 |
| 4 ml | 175 | 676 | 23.62 |
| 5 ml | 177 | 853 | 23.35 |
| 1–5 ml | 853 | — | 24.23 |
| 2–5 ml | 692 | — | 23.89 |

It is evident from Tables 1–4 that as every etching procedure is carried out, the etching rate becomes slower, indicating that the etching ability becomes lower. Since the etching rate can be easily and accurately determined by the etching rate measuring method of the present invention, the invention facilitates the management of the etchant in an etching process.

As described above, the method and apparatus for determining the etching rate according to the present invention permits accurate determination of the etching rate with a relatively simple arrangement, enabling secure and low-cost management of the etchant in an etching process.

While there has been described herein what is considered to be a preferred embodiment of the present invention, other modifications of the invention shall be apparent to those skilled in the art from the teaching herein and it is, therefore, desired to secured in the appended claims all such modifications as fall within the true spirit and scope of the invention.

We claim:

1. A method for determining the etching rate at which a metal part is etched with an acid or alkali etchant in an etching tank, wherein said metal part generates hydrogen gas when etched with said etchant, comprising:

(A) providing an apparatus comprising an etching tank containing etchant, a reaction column, a metering column, and a priming column, wherein said reaction column is in fluid communication with said etching tank, said priming column and said metering column are in fluid communication with said reaction column, and said metering column is in fluid communication with said etching tank;

(B) determining the unit quantity hydrogen release time, comprising:

(1) evacuating air from said priming column, thereby channelling etchant into said reaction column from said etching tank, and channelling etchant from said reaction column into said priming column, until said reaction column is filled with etchant and said priming column contains a predetermined level of etchant, (2) evacuating air from said metering column, thereby channelling etchant from said reaction column into said metering column until said metering column contains a predetermined initial level of etchant and said reaction column is full of etchant, (3) pressurizing said metering column, thereby forcing etchant into said etching tank, until said metering column contains a predetermined final level of etchant which is lower than said predetermined initial level, (4) etching a specimen of the same material to be etched with the etchant in said reaction column, thereby generating hydrogen gas, pressurizing said reaction column and purging etchant to said metering column, thereby increasing the level of etchant in said metering column, (5) measuring the time beginning with said etching and ending when the level of etchant in said metering column again reaches said predetermined initial level; and (C) computing the etching rate from said unit quantity hydrogen release time.

2. An apparatus for determining the etching rate at which a metal part is etched with an acid or alkali etchant in an etching tank, wherein said metal part generates hydrogen gas when etched with said etchant, said apparatus comprising a reaction column of the closed type adapted to accommodate therein a specimen of the same material as said metal part to be etched in said etching tank and to receive said etchant from said etching tank, whereby said specimen is subjected to etching with said etchant in said reaction column, a metering column connected to said reaction column such that said etchant is introduced into said metering column from said reaction column as the interior pressure of said reaction column increases, a flow control mechanism for controlling the inflow and outflow of said etchant into and from the respective columns, said flow control mechanism operating to channel said etchant from said etching tank to said reaction column, whereby said specimen is subjected to etching with said etchant in said reaction column whereupon said etchant is channeled from said reaction column into said metering column due to an increase in the interior pressure of said reaction column as a result of said hydrogen gas generation during said etching, and means for measuring the time taken until said etchant in said metering column reaches a predetermined quantity.

3. An apparatus for determining the etching rate at which a metal part is etched with an acid or alkali etchant in an etching tank, wherein said metal generates hydrogen gas when etched with said etchant, comprising:

(A) an etching tank;
(B) a closed box reaction column adapted to accommodate a specimen of the same material as a metal part to be etched in said etching tank, comprising:
  (1) a top and a bottom, and
  (2) an etchant inlet line comprising a distal end and a proximal end, wherein said distal end is immersed in etchant in said etching tank, and wherein said proximal end is attached to said bottom of said reaction column;
(C) a cylindrical metering column comprising:
  (1) a top and a bottom,
  (2) a feed line comprising a proximal end and a distal end, wherein said proximal end is attached to said bottom of said cylindrical column and said distal end is in communication with a bottom of said reaction column,
  (3) a return line comprising a proximal end and a distal end, wherein said proximal end is at a level inside said metering column, and said distal end is disposed above said etching tank,
  (4) a liquid level sensor comprising a sensing end located at a level above the level of said proximal end of said return line, and
  (5) a first air pump coupled to said top of said metering column;
(D) a priming column comprising:
  (1) a top and a bottom,
  (2) a line comprising a proximal end and a distal end, wherein said proximal end is attached to said bottom of said priming column, and said distal end is attached to said top of said reaction column,
  (3) a first liquid level sensor comprising a sensing end located at a level inside said priming column, and
  (4) a second air pump coupled to said top of said priming column.

4. An apparatus for determining the etching rate at which a metal part is etched with an acid or alkali etchant in an etching tank, wherein said metal generates hydrogen gas when etched with said etchant, comprising:

(A) an etching tank;
(B) a closed box reaction column adapted to accommodate a specimen of the same material as a metal part to be etched in said etching tank, comprising:
  (1) a top and a bottom, and
  (2) an etchant inlet line comprising a distal end and a proximal end, wherein said distal end is immersed in etchant in said etching tank, and wherein said proximal end is attached to said bottom of said reaction column;
(C) a cylindrical metering column comprising:
  (1) a top and a bottom,
  (2) a feed line comprising a proximal end and a distal end, wherein said proximal end is attached to said bottom of said cylindrical column and said distal end is in communication with a bottom of said reaction column,
  (3) a return line comprising a proximal end and a distal end, wherein said proximal end is at a level inside said metering column, and said distal end is disposed above said etching tank,
  (4) a liquid level sensor comprising a sensing end located at a level above the level of said proximal end of said return line, and
  (5) a first air pump coupled to said top of said metering column, comprising:
    (a) a pump body having a suction end and a discharge end,
    (b) a loop line connecting said suction end to said discharge end,
    (c) a suction end valve and a discharge end valve disposed in said loop line near said suction end and said discharge end, respectively,
    (d) a coupling line having a proximal end connected to said loop line between said suction end valve and said discharge end valve, and a distal end connected to said metering column,
    (e) an air venting valve connected to said coupling line, such that when said air venting valve is closed, said discharge end valve is closed, and said suction end valve is open, said air pump functions as a suction pump, and when said air venting valve is closed, said discharge end valve is open, and said suction end valve is closed, said air pump functions as a discharge pump;

(D) a priming column comprising:
  (1) a top and a bottom,
  (2) a line comprising a proximal end and a distal end, wherein said proximal end is attached to said bottom of said priming column, and said distal end is attached to said top of said reaction column,
  (3) a first liquid level sensor comprising a sensing end located at a level inside said priming column, and
  (4) a second air pump coupled to said top of said priming column comprising:
    (a) a pump body having a suction end and a discharge end,
    (b) a loop line connecting said suction end to said discharge end,
    (c) a suction end valve and a discharge end valve disposed in said loop line near said suction end and said discharge end, respectively,
    (d) a coupling line having a proximal end connected to said loop line between said suction end valve and said discharge end valve, and a distal end connected to said priming column,
    (e) an air venting valve connected to said coupling line, such that when said air venting valve is closed, said discharge end valve is closed, and said suction end valve is open, said air pump functions as a suction pump, and when said air venting valve is closed, said discharge end valve is open, and said suction end valve is closed, said air pump functions as a discharge pump.

* * * * *